US00PP11932P2

(12) United States Plant Patent
Kientzler

(10) Patent No.: US PP11,932 P2
(45) Date of Patent: Jun. 19, 2001

(54) NEW GUINEA IMPATIENS PLANT NAMED 'KICAP'

(75) Inventor: Ludwig Kientzler, Gensingen (DE)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/439,351

(22) Filed: Nov. 15, 1999

(51) Int. Cl.[7] ..... A01H 5/00
(52) U.S. Cl. ..... Plt./318
(58) Field of Search ..... Plt./318

(56) References Cited

PUBLICATIONS

GTITM UPOVROM Citation for 'Kicap' as per CA PBR 99–1714; Jun. 15, 1999.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of New Guinea Impatiens plant named 'Kicap', characterized by its large purple and lavender bi-colored flowers; upright to outwardly spreading, compact growth habit; freely branching, dense and bushy plant habit; and dark green leaves with red-colored veins.

1 Drawing Sheet

BACKGROUND OF THE INVENTION

The present invention relates to a new and distinct cultivar of New Guinea Impatiens plant, botanically known as *Impatiens hawkeri*, and hereinafter referred to by the cultivar name 'Kicap'.

The new cultivar is a product of a planned breeding program conducted by the Inventor in Gensingen, Germany. The objective of the breeding program was to develop early-flowering varieties with numerous flowers, freely-branching and uniform plant habit, attractive flower and foliage colors, and good flower form.

The new cultivar originated from a cross made by the Inventor of the proprietary selection identified as LB662 as the male, or pollen parent, with the proprietary selection identified as B26as the female, or seed parent.

The cultivar 'Kicap' was discovered and selected by the Inventor as a flowering plant within the progeny of the stated cross in a controlled environment in Gensingen, Germany, in April, 1997.

Asexual reproduction of the new cultivar by terminal cuttings taken at Gensingen, Germany, has shown that the unique features of this new cultivar are stable and reproduced true to type in successive generations of asexual reproduction.

SUMMARY OF THE INVENTION

The following traits have been repeatedly observed and are determined to be the unique characteristics of 'Kicap'. These characteristics in combination distinguish 'Kicap' as a new and distinct cultivar:

1. Large purple and lavender bi-colored flowers.
2. Upright to outwardly spreading, compact growth habit.
3. Freely branching, dense and bushy plant habit.
4. Dark green leaves with red-colored veins.

Plants of the new cultivar can be compared to plants of the commercial cultivar 'Octavia', disclosed in U.S. Plant Pat. No. 8,430. However, in side-by-side comparisons conducted in Encinitas, Calif., plants of the new cultivar differ from plants of the cultivar 'Octavia' in the following characteristics:

1. Plants of the new cultivar are smaller, more compact, less vigorous and more uniform than plants of the cultivar 'Octavia'.
2. Flowers of plants of the new cultivar are more round and flatter than flowers of plants of the cultivar 'Octavia'.
3. Flowers of plants of the new cultivar have a lighter lavender background color than flowers of plants of the cultivar 'Octavia'.
4. Plants of the new cultivar flower about 10 to 14 days earlier than plants of the cultivar 'Octavia'.

A detailed comparison of plants of the cultivars 'Kicap' and 'Octavia' appears in Chart A at the end of the specification.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical plant of the cultivar 'Kicap'.

The photograph at the bottom of the sheet comprises a comparison close-up view of typical flower buds, flowers and upper and lower surfaces of leaves of the cultivars 'Kicap' (left) and 'Octavia' (right). Flower and foliage colors in the photographs may differ from the actual colors due to light reflectance.

DETAILED BOTANICAL DESCRIPTION

Plants of the cultivar 'Kicap' have not been observed under all possible environmental conditions. The phenotype may vary somewhat with variations in environment such as temperature and light intensity, without, however, any variance in genotype. The following observations, measurements and comparisons describe plants grown in 25-cm hanging baskets in Encinitas, Calif., under commercial practice in a polyethylene-covered greenhouse with day temperatures averaging 23° C., night temperatures averaging 19° C., and light levels about 3,000 foot-candles. Plants were about 17 weeks old after planting a rooted cutting.

In the following description, color references are made to The Royal Horticultural Society Colour Chart except where general terms of ordinary dictionary significance are used.

Classification:

*Botanical.*—*Impatiens hawkeri* cultivar 'Kicap'.

*Commercial.*—New Guinea Impatiens cultivar 'Kicap'.

Parentage:

*Male parent.*—Proprietary selection of *Impatiens hawkeri* identified as LB662.

*Female parent.*—Proprietary selection of *Impatiens hawkeri* identified as B26.

Propagation:

*Type cutting.*—Terminal cuttings.

*Time to initiate roots.*—About 10 days with 20° C. soil temperature.

*Time to develop roots.*—About 21 days with 20° C. soil temperature.

*Root description.*—Fine and fibrous.

Plant description:

*Plant form.*—Upright to outwardly spreading; V-shaped; compact.

*Growth habit.*—Moderately vigorous. Freely branching, dense and bushy growth. Appropriate for 10 to 25-cm containers.

*Crop time.*—For finished flowering plants grown in a 10-cm container, about 8 to 10 weeks from rooted cuttings are required; for finished flowering plants grown in a 25-cm container, about 17 weeks from rooted cuttings are required.

*Plant size.*—Height: About 17 cm. Width or spread: About 28 cm.

*Lateral branches.*—Quantity: About 7. Length: About 12 cm. Diameter: About 7 mm. Internode length: About 2 cm. Color: 59B to 59C.

*Foliage description.*—Leaves simple, generally symmetrical, abundant, opposite or in whorls, horizontal to plant. Mostly flat. Length: About 8.5 cm. Width: About 4.25 cm. Shape: Elliptic. Apex: Acuminate. Base: Attenuate. Margin: Serrulate with ciliation. Texture: Rugose; somewhat glossy. Color: Young foliage, upper surface: 137A. Young foliage, lower surface: 59A. Fully expanded foliage, upper surface: 147A. Fully expanded foliage, lower surface: 59A. Venation, upper surface: 59A. Venation, lower surface: 59B. Petiole: Length: About 2.5 cm. Diameter: About 4 mm. Color: 60B.

Flower description:

*Flower type and habit.*—Purple and lavender bi-colored flowers. Freely and continuously flowering. Flowers arise from leaf axils. Usually about 10 flowers and flower buds per lateral branch. Flowers positioned above the foliage and face upward and outward. Flowers nearly round and mostly flat. Flowers persistent.

*Flowering season.*—Year-round under greenhouse conditions. In the garden, flowering is continuous from spring until fall.

*Flower size.*—Length: About 5.5 cm. Width: About 5.2 cm. Depth: About 1.4 cm.

*Flower buds.*—Length: About 1.6 cm. Diameter: About 1 cm. Shape: Ovoid. Color: 63A.

*Petals.*—Quantity: Five. Length: Upper petal: About 2.5 cm. Middle petals: About 2.4 cm. Lower petals: About 2.8 cm. Width: Upper petal: About 3.8 cm. Middle petals: About 2.5 cm. Lower petals: About 2.8 cm. Shape: Cordate. Apex: Cordate. Base: Acute. Margin: Entire. Texture: Velvety, smooth. Color: When opening, upper surface: 68A; apex, 66A. When opening, lower surface: 68B and 66C. Fully opened, upper surface: Background, 68B; base and central areas/lines, 74A. Fully opened, lower surface: 68B and 68A.

*Spur.*—Length: About 4.75 cm. Shape: Narrow and curved. Color: At petal base, 50D; apex, 1B to 1C.

*Peduncles.*—Length: About 5.7 cm. Angle: About 60° from vertical. Strength: Strong. Color: 145B.

*Reproductive organs.*—Androecium: Stamen number: Five, anthers fused, filaments free. Anther shape: Obovate. Anther size: 3 mm by 5 mm. Anther color: 4D. Amount of pollen: Moderate. Pollen color: 4D. Gynoecium: Five-loculate fused. Pistil number: One. Pistil length: About 4 mm. Stigma color: 63A. Ovary color: 59B.

Disease resistance: Under commercial conditions, resistance to pathogens common to New Guinea Impatiens has not been observed.

Seed development: Seed production has not been observed.

CHART A

| CHARACTERISTIC | 'KICAP' | 'OCTAVIA' |
|---|---|---|
| PLANT HEIGHT | About 17 cm | About 26 cm |
| PLANT WIDTH | About 28 cm | About 33 cm |
| VIGOR | Moderate | Vigorous |
| LEAF LENGTH | About 8.5 cm | About 9.75 cm |
| LEAF WIDTH | About 4.25 cm | About 4.5 cm |
| PETAL COLOR, MATURE, UPPER SURFACE | Background, 68B; base and central areas/lines, 74A | Background, 78C; base and central areas/lines, 66B |
| PETAL COLOR, MATURE, LOWER SURFACE | 68B and 68A | 67C and 50A |
| SPUR COLOR | At petal base, 50D; 1B to 1C at apex | 2D |
| PEDUNCLE COLOR | 145B | 62C to 62D |

It is claimed:

1. A new and distinct cultivar of New Guinea Impatiens plant named 'Kicap', as illustrated and described.

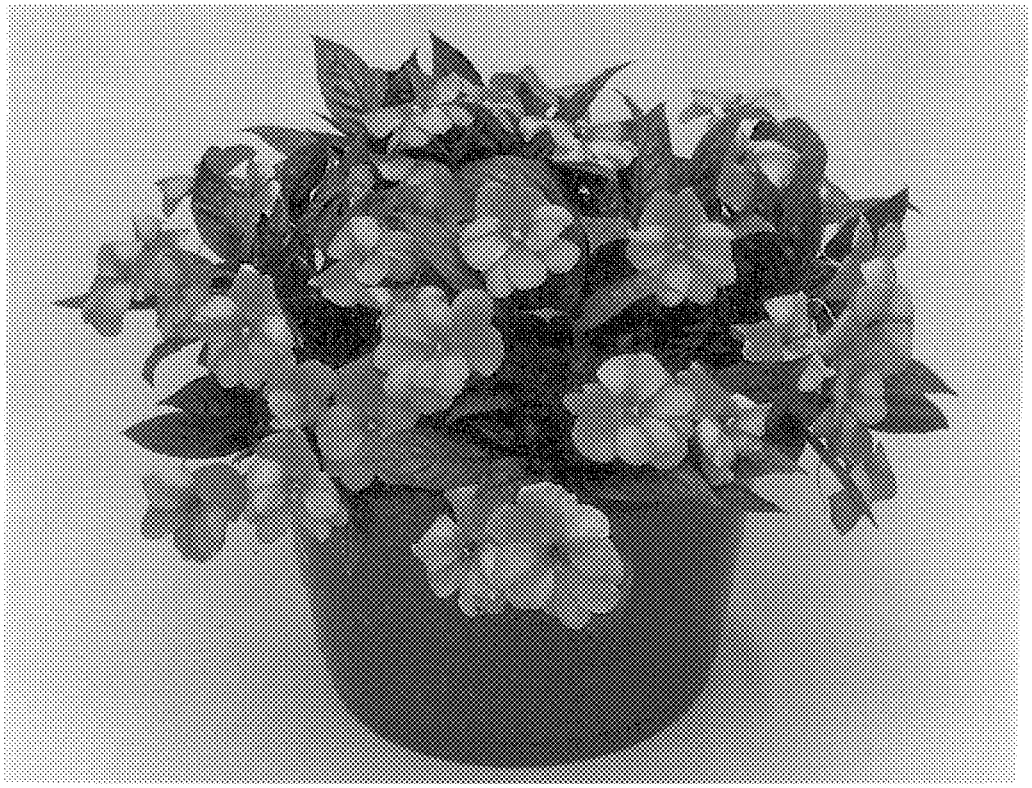
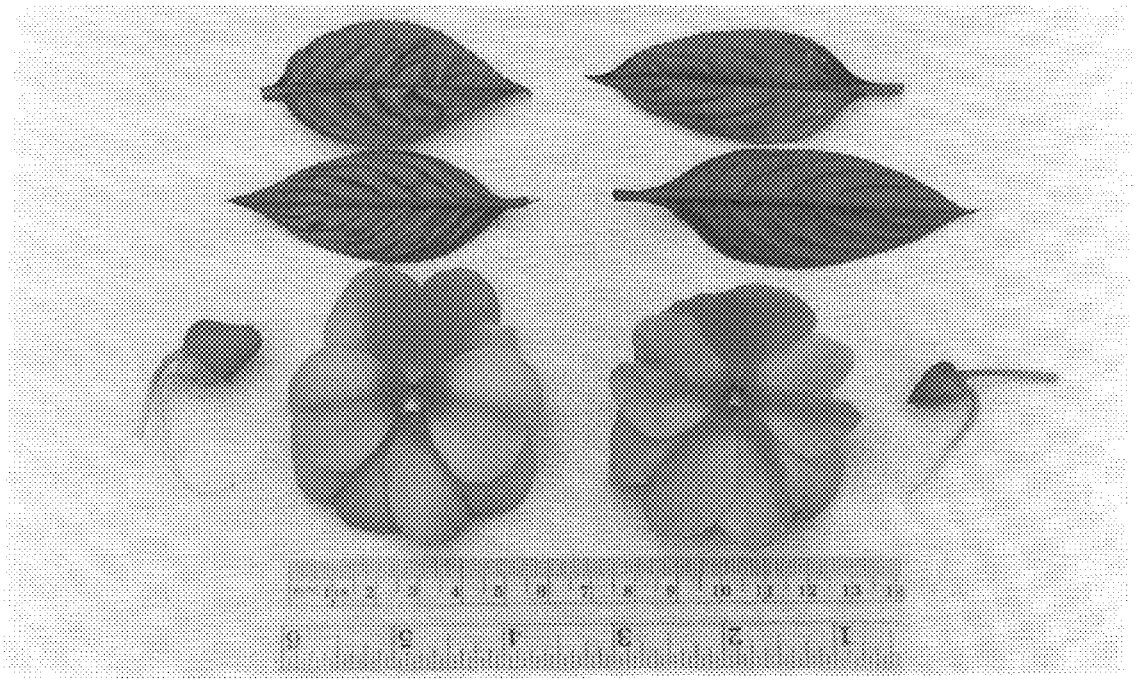

* * * * *